(12) United States Patent
Bradshaw et al.

(10) Patent No.: US 6,897,353 B2
(45) Date of Patent: May 24, 2005

(54) YEAST-BACTERIA SHUTTLE VECTOR

(75) Inventors: M. Suzanne Bradshaw, Cincinnati, OH (US); Jacques A. Bollekens, Brussels (BE); Frank H. Ruddle, New Haven, CT (US)

(73) Assignee: Yale University, New Haven, CT (US)

( * ) Notice: Subject to any disclaimer, the term of this patent is extended or adjusted under 35 U.S.C. 154(b) by 296 days.

(21) Appl. No.: 09/729,043

(22) Filed: Dec. 4, 2000

(65) Prior Publication Data

US 2002/0132348 A1 Sep. 19, 2002

Related U.S. Application Data

(63) Continuation of application No. 09/095,372, filed on Jun. 10, 1998, now Pat. No. 6,221,588, which is a continuation of application No. 08/761,704, filed on Dec. 6, 1996, now Pat. No. 5,866,404.
(60) Provisional application No. 60/008,250, filed on Dec. 6, 1995.

(51) Int. Cl.⁷ .......................... C12N 15/00; C12N 1/14
(52) U.S. Cl. ........................ 800/21; 435/254.2; 800/25
(58) Field of Search .............................. 800/25, 18, 22; 435/254.1, 6, 91.4, 476, 477, 483

(56) References Cited

PUBLICATIONS

Strauss et al. Expression of the beta subunit of chorionic gonadotropin in transgenic mice. JBC, 1994, vol 296, No. 7, pp. 4968–4973.*
Bradley et al. Modifying the Mouse: Design and Desire. May 1992. Biotechnology. vol. 10, pp. 534–539.*
Campbell and Wilmut. Totipotency of Multipotentiality of Cultured Cells: Applications and Progress. Theriogenology. Jan. 1, 1997. vol. 47, No. 1, pp. 63–70.*
Mullins and Mullins. Perspective Series: Molecular Medicine in Genetically Engineered Animals. Apr. 1, 1996. Clinical Investigation. vol. 97, No. 7, pp. 1557–1560.*
Kogoma, Tokio, "Stable DNA Replication: Interplay between DNA Replication, Homologous Recombination, and Transcription", *Microbiology and Mole. Bio.,* vol. 61, No. 2., pp. 212–238, Jun. 1997.
Larionov, Vladimir, et al., "Direct isolation of human BRCA2 gene by tranformation–associated recombination in yeast", *Proc. Natl. Acad, Sci., USA,* vol. 94, pp. 7384–7387, Jul. 1997.
van Dijk, et al., "A Functional Assay in Yeast for the human Estrogen Receptor Displays Wild–Type and Variant Estrogen Receptor Messenger RNAs Present in Breast Carcinoma", *Cancer Research,* 57, pp. 3478–3485, Aug. 15, 1997.
Frengen, et al., "Transfer of small YACs to *E. coli.* as large circular plasmids", *Genetic Analysis Biomolecular Engineering,* 14, pp. 57–59, 1997.

Larionov, Vladimir, et al., "Specific cloning of human DNA as yeast artificial chromosomes by transformation–associates recombination", *Proc. Natl. Acad. Sci., USA,* vol. 93., pp. 491–496, Jan. 1996.
Bradshaw, Suzanne, M., et al., "A long–range regulatory element of Hoxc8 identified by using the pClasper vector", *Proc. Natl. Acad. Sci., USA,* vol. 93, pp. 2426–2430, Mar. 1996.
Simpson, Kaetrin, et al., "A shuttle system for transfer of YACs between yeast and mammalian cells", *Nucleic Acids Research,* vol. 24, No. 23, pp. 4693–4699, 1996.
Bradshaw, Suzanne M., et al. "A new vector for recombination–based cloning of large DNA fragments from yeast artificial chromosomes", *Nucleic Acids Research,* vol. 23, No. 23, pp. 4850–4856, 1995.
Campbell, Colin, et al., "Unequal homologous recombination of human DNA on a yeast artificial chromosome", *Nucleic Acids Research,* vol. 23, No. 18, pp. 3691–3695, 1995.
Ketner, Gary, et al., "Efficient manipulation of the human adenovirus genome as an infectious yeast artificial chromosome clone", *Proc. Natl. Acad. Sci., USA,* vol. 91, pp. 6186–6190, Jun. 1994.
Kouprina, N., et al., "A Model System to Assess the Integrity of Mammalian YACs during Transformation and Propagation in Yeast", *Genomics,* 21, pp. 7–17, 1994.
Larionov, V., et al., Recombination during transformation as a source of chimeric mammalian artificial chromosomes in yeast (YACs), *Nucleic Acids Research,* vol. 22, No. 20, pp. 4154–4162, 1994.
Miller, Leilani, et al., "lin–31, a *Caenorhabditis elegans* HNF–3/fork head transcription factor homolog, specifies three alternative cell fates in vulval development", *Genes and Development,* vol. 7, pp. 933–947, 1993.
Bradshaw, Suzanne M., et al., "Site Specific Recombination–Mediated Isolation of a Large Sub–Region from a Mouse Hox–c YAC", Ist Euro. Sci. Found. Conf. On Deve. Biol., Karause Ittengen, Switzerland, Jun. 14–17, 1993.
Pavan, William, et al., "Generation of deletion derivatives by targeted transformation of human–derived yeast artificial chromosomes", *Proc. Natl. Acad. Sci., USA.,* vol. 87, pp. 1300–1304, Feb. 1990.
Sikorski, Robert S., et al., "A System of Shuttle Vectors and Yeast Host Strains Designed for Efficient Manipulation of DNA in *Saccharomyces cerevisiae*", Genetics, vol. 122, pp. 19–27, May 1989.

(Continued)

Primary Examiner—Anne-Marie Falk
Assistant Examiner—Celine Qian

(57) ABSTRACT

The functional analysis of genes frequently requires the manipulation of large genomic regions. A yeast-bacteria shuttle vector is described, that can be used to clone large regions of DNA by homologous recombination. The important feature of present invention is the presence of the a bacterial replication origin, which allows large DNA insert capacity. The utility of this vector lies in its ability to isolate, manipulate and maintain large fragments in bacteria and yeast, allowing for mutagenesis by yeast genetics and simplified preparation of plasmid DNA in bacteria.

10 Claims, 5 Drawing Sheets

Burgers, Peter, M.J., et al., "Transformation of Yeast Spheroplasts without Cell Fusion", Analytical Biochemistry, vol. 163, pp. 391–397, 1987.

Orr–Weaver, Terry L., et al., "Genetic Applications of Yeast Transformation with Linear and Gapped Plasmids", Methods in Enzymology, vol. 101, pp. 228–245, 1983.

Orr–Weaver, Terry L., et al., "Yeast recombination: The association between double–strand gap repair and crossing–over", *Proc. Natl. Acad. Sci., USA,* vol. 80, pp. 4417–4421, Jul. 1983.

Orr–Weaver, Terry L., et al., "Yeast transformation: A model system for the study of recombination", *Proc. Natl. Acad. Sci., USA,* vol. 78, No. 10, pp. 6354–6358, Oct. 1981.

Boyd, E.F., and Hartl, D.L. (1997). Recent horizonal transmission of plasmids between natural populations of *Escherichia coli* and *Salmonella enterica*. *Journal of Bacteriology* 179, pp. 1622–1627.

Campbell, C., Gulati, R., Nandi, A. K., Floy, K., Hieter, P., and Kucherlapati, R. S. (1991). Generation of a nested series of interstitial deletions in yeast artificial chromosomes. *Proc. Natl. Acad. Sci. USA* 88, pp. 5744–5748.

Degryse, E., Dumas, B., Dietrich, M., Laruelle, L., and Ascstetter, T. (1995). In vivo cloning by homologous recombination in yeast using a two–plasmid–based system. *Yeast* 11, pp. 629–640.

McGonigal, T., Bodelle, P., Schopp, C., and Sarthy, A.V. (1995). Construction of a human DNA library in a circular centromere–based yeast plasmid. *Gene* 155, pp. 267–271.

Prado, F., and Aguilera, A. (1994). New in–vivo cloning methods by homologous recombination in yeast. *Current Genetics* 25, pp. 180–183.

Spencer, F., Ketner, G., Connelly, C., and Hieter, P. (1993). Targeted recombination–based cloning and manipulation of large DNA segments in yeast. *Methods: A companion to Methods Enzymol* 5, pp. 161–175.

Hermanson, G. G., Hoekstra, M. F., McElligott, D. L., and Evans, G. A. 1(1991). Rescue of end fragments of yeast artificial chromosomes by homologous recombination in yeast. *Nucl. Acids Res.* 18, pp. 4943–4948.

Herzing, L. B. K., and Ashworth, A. (1995). Construction of specific cosmids from YACs by homologous recombination in yeast. *Nucl. Acids Res.* 19, pp. 4005–4006.

Larionov, V., Kouprina, N., Graves, J., and Resnick, M. A. (1996). Highly selective isolation of human DNAs from rodent–human hybrid cells as circular yeast artificial choromosomes by transformation–associated recombination cloning, *Proceedings of the National Academy of Sciences of the United States of America* 93, pp. 13925–13930.

Emmanuel, S. L., Cook, J. R., O'Rear, J., Rothstein, R., and Petska, S. (1995). New vectors for manipulation and selection of functional yeast artificial chromosomes (YACs) containing DNA inserts. *Gene* 155, pp. 167–174.

Erickson, J. R., and Johnston, M. (1993). Direct cloning of yeast genes from an ordered set of lambda clones in *Saccharomyces cerevisiae* by recombination in vivo. *Genetics* 134, pp. 151–157.

Fairhead, C., Llorente, B., Denis, F., Soler, M., and Dujon, B. (1996). New vectors for combinatorial deletions in yeast chromosomes and for gap–repair cloning using 'split–marker' recombination. *Yeast* 12, pp. 1439–1457.

\* cited by examiner

SEQUENCE LISTING

<160> NUMBER OF SEQ ID NOS: 13

<210> SEQ ID NO 1
<211> LENGTH: 25
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 1
tagatctgtt tgtctcccac atgcc                                    25

<210> SEQ ID NO 2
<211> LENGTH: 25
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 2
aggtggcagg ataaggaagg gttag                                    25

<210> SEQ ID NO 3
<211> LENGTH: 24
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 3
cgacaaggaa caaatcctaa gccc                                     24

<210> SEQ ID NO 4
<211> LENGTH: 24
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 4
tgcatttgca gcctgatcca gcca                                     24

<210> SEQ ID NO 5
<211> LENGTH: 22
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 5
tctcatgttt gacagcttat ca                                       22

```
<210> SEQ ID NO 6
<211> LENGTH: 25
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 6
agagtatact acataacata acaca                                         25

<210> SEQ ID NO 7
<211> LENGTH: 23
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 7
ttcaagggaa ttgatcctct acg                                           23

<210> SEQ ID NO 8
<211> LENGTH: 21
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 8
aagattccga ataccgcaag c                                             21

<210> SEQ ID NO 9
<211> LENGTH: 22
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 9
ttaaagaacg tggactccaa cg                                            22

<210> SEQ ID NO 10
<211> LENGTH: 23
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 10
actgtgctct gcagtctcat ccg                                           23

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 11
cgcagcggtc gacaaactta ca                                            22

<210> SEQ ID NO 12
<211> LENGTH: 24
<212> TYPE: DNA
<213> ORGANISM: ARTIFICIAL SEQUENCE
<220> FEATURE:
<223> OTHER INFORMATION: OLIGONUCLEOTIDE
```

-continued

```
<400> SEQUENCE: 12
ctcctcctct ttctcctctt ccta                                          24

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 13
caacttggct accgagagta                                               20
```

US 6,897,353 B2

YEAST-BACTERIA SHUTTLE VECTOR

This is a continuation of application Ser. No. 09/095,372, filed Jun. 10, 1998 now U.S. Pat. No. 6,221,588 which is a continuation of application Ser. No. 08/761,704, filed Dec. 6, 1996 now U.S. Pat. No. 5,866,404, which is a continuation-in-part of U.S. Provisional Application Ser. No. 60/008,250 filed Dec. 6, 1995. +gi

STATEMENT OF GOVERNMENT SUPPORT

This invention was made with Government support under Contract Nos. GM09966, DK02018, and HD07477 awarded by the National Institutes of Health. The Government of the United States of America has certain rights in this invention.

FIELD OF THE INVENTION

The present invention relates to the field of genomics and the ability to manipulate, isolate and replicate large fragments of DNA.

BACKGROUND OF THE INVENTION

For the functional analysis of many genes investigators need to isolate and manipulate large DNA fragments. The advent of genomics and the study of genomic regions of DNA has generated a need for vectors capable of carrying large DNA regions.

In general, two types of yeast vector systems are presently available. The first type of vector is one capable of transferring small insert DNA between yeast and bacteria (33, 34). A second type of vector is a fragmenting vector which creates interstitial or terminal deletions in YACs (35, 36, 37). The small insert shuttle vectors are able to recombine with and recover homologous sequences. They are centromere-based and replicate stably and autonomously in yeast, but also contain a high-copy origin of replication for maintenance as bacterial plasmids. However, these vectors are limited by their small insert capacity.

The second type of vector, known as fragmenting vectors, also have recombinogenic sequences but are unable to transfer the recovered insert DNA to bacteria for large preparations of DNA.

Researchers use fragmentation techniques to narrow down the region of interest in YACs (1, 2). However, isolating sufficient quantities of YAC DNA from agarose gels for microinjection or electroporation remains cumbersome. Purification remains a problem when the YAC comigrates with an endogenous chromosome. In addition, YACs may be chimeric or contain additional DNA regions that are not required for the particular functional study.

Types of vectors available for cloning large fragments in bacteria are cosmids, Pls and BACS. These vectors are limited to bacteria and cannot be shuttled to yeast for modification by homologous recombination.

One object of the present invention relates to the identification of a new yeast-bacteria shuttle vector capable of accommodating large fragments of DNA.

Another object of the present invention relates to the use of the new yeast bacteria shuttle vector for cloning large DNAs.

Yet another object of the present invention relates to the use of the new yeast bacteria for site-specific targeting of genomic DNA.

SUMMARY OF THE INVENTION

A new yeast-bacteria shuttle vector has been identified that allows selective cloning and/or manipulation of large regions of DNA. The vector of the present invention provides a unique combination of features including site-specific targeting, yeast to bacteria (and bacteria to yeast) shuttling capability, interchangeable recombinogenic ends, large insert capacity, and near universal compatibility with large insert cloning systems in bacteria and yeast. When combined with a method for direct cloning of co-transformed genomic DNA, the vector of the present invention provides a highly versatile cloning system.

The circular product of cloning in the present vector can be transferred to bacteria for simplified preparation of large quantities of plasmid DNA. The shuttle capability of the vector makes mutagenesis techniques by yeast genetics accessible for the production of large reporter constructs. The yeast bacterial shuttle vector of the present invention comprises a yeast replication origin, a yeast selection marker gene, a bacteria replication origin, a bacteria selection marker gene and at least one unique cloning site.

One embodiment of the present invention combines the single-copy F factor replicon and chloramphenicol resistance gene for stable propagation of large circular DNA in bacteria with the CEN6/ARS4 origin of replication and LEU2 gene for maintenance and selection in yeast. This vector is called pCLASPER. The bacterial origin of replication chosen is the one used in bacterial artificial chromosomes (BACs). Recognition sites for two intron-encoded endonucleases have been engineered to flank an unique polylinker. This vector has been used to clone various regions.

DETAILED DESCRIPTION OF THE INVENTION

Figure 1:
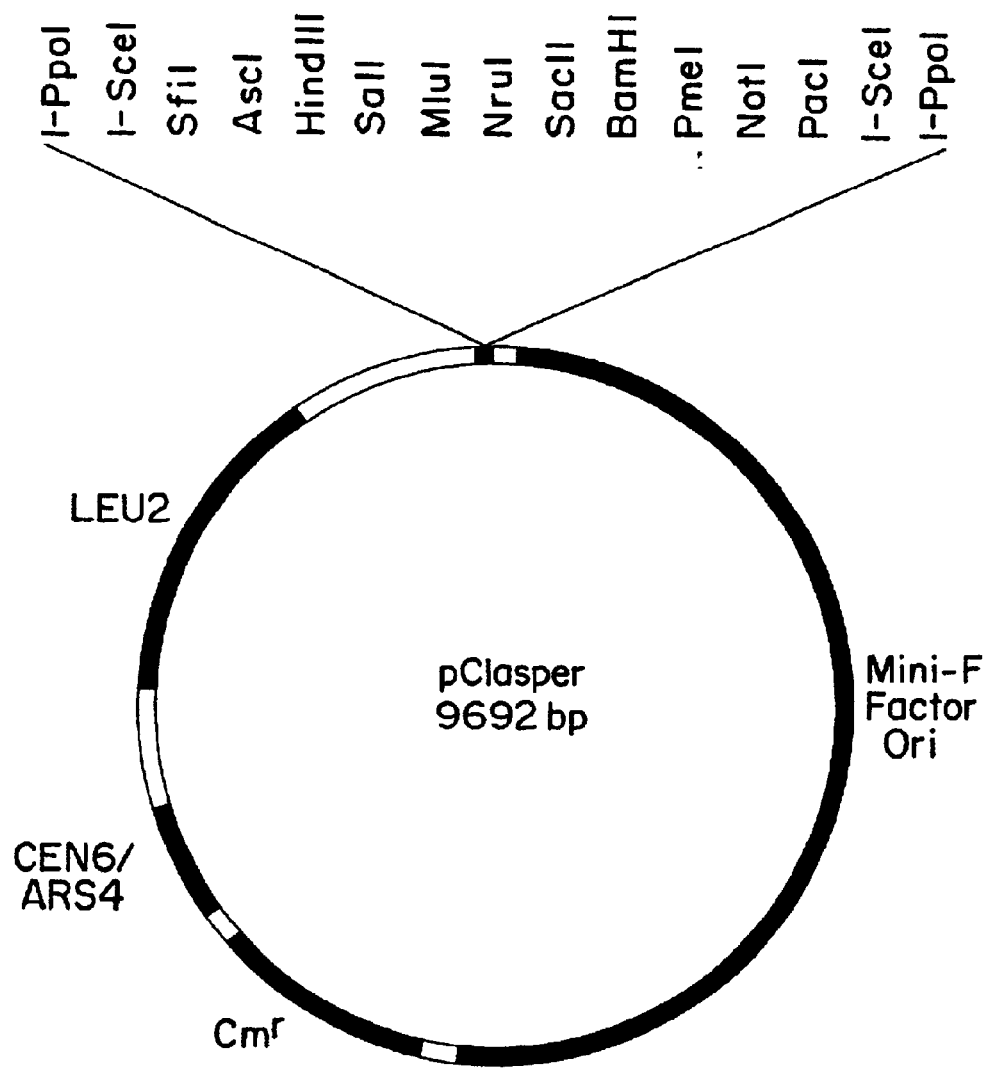
FIG. 1. Schematic representation of pCLASPER vector. Relative positions of the yeast LEU2 gene and CEN6/ARS4 sequences and the bacterial chloramphenicol resistance (Cm$^r$) gene and mini-F factor origin of replications are shown. Unique restriction enzyme sites in the polylinker are indicated above. Unfilled lines are sequences carried from the parental vectors from which the above mentioned genes were cloned as described in the materials and methods.

The present invention relates to a new vector design capable of manipulating large pieces of DNA. The vector of the present invention is a yeast-bacteria shuttle vector.

The yeast bacterial shuttle vector of the present invention comprises a yeast replication origin, a yeast selection marker gene, a bacteria replication origin, a bacteria selection marker gene and at least one unique cloning site. The yeast replication origin is used for replication and propagation in yeast. Examples of such elements are any of the known yeast autonomous replicating sequences (ARS) or centromeres (CEN). The yeast selection marker gene may be selected from a known gene capable of being selected for: such genes include but are not limited to genes encoding auxotrophic markers, such as LEU2, HIS3, TRP1, URA3, ADE2 and LYS2. Alternatively, genes encoding a protein conferring drug resistance on a host cell can be used as a yeast selection marker. Such genes include, but are not limited to CAN1 and CYH2. The bacterial replication origin is preferably selected from those replication origins used for stable bacterial replication of large DNA inserts, including the F factor and the P1 replicon. Any of the many known bacterial selection marker genes may be used; examples of bacterial selection marker genes include genes conferring bacterial resistance to antibiotics, such as kanamycin, ampicillin, tetracycline, Zeocin, neomycin and hygromycin and chloramphenicol. Other antibiotic resistance genes are encompassed herein and are known to those skilled in the art.

The yeast bacteria shuttle vector of the present invention represents a combinations of several vector features: 1) site-specific targeting, 2) yeast to bacteria (and bacteria to yeast) shuttle capability, 3) interchangeable recombinogenic ends, 4) large insert capacity, and 5) near universal compatibility with large insert cloning systems in bacteria and yeast.

The yeast bacteria shuttle vector has recombinogenic ends specific to regions in genomic DNA. Yeast cells containing YACs are transformed with the linearized vector. Alternatively, genomic DNA is co-transformed with the linearized vector into yeast. By homologous recombination in yeast, the target region is rescued in the yeast bacteria shuttle vector and can be shuttled to bacteria for amplification.

The yeast bacteria shuttle vector of the present invention is useful as a vehicle to shuttle genomic DNA into bacteria for further analysis, such as isolation, mutation, cloning or amplification.

One embodiment of the present invention is a vector, known as pCLASPER. The DNA sequence of the vector is provided in GenBank, under Accession No. U38900.

In one embodiment of the present invention, the vector known as pCLASPER was designed using as the bacterial origin of replication the F factor genes for replication and copy number control, oriS, repE, parA and parB. This is the minimal region, previously referred to as the mini-F factor, required for stable maintenance of single-copy plasmids. The same regions of the F factor are used in bacterial artificial chromosomes (BACs; 3) which have been shown to maintain exogenous DNA inserts of up to 300 kb in bacteria. To this, the chloramphenicol resistance gene, the yeast CEN6/ARS4 origin of replication and LEU2 gene for selection in yeast were added. Also added, was an extensive polylinker flanked by recognition sites for two intron-encoded endonucleases. Examples of such intron-encoded endonucleases include but are not limited to I-Ppol and I-Scel. Endonucleases restriction sites useful in the vector of the present invention may vary in size. The endonucleases I-Ppol and I-Scel, for example, have 18 bp recognition sites and were useful in the construction of the pCLASPER vector for removing vector sequence from very large inserts.

The mitotic and structural stability of this example vector was found to be equivalent to the parental yeast vector, pRS415 (20), and to a similar bacterial vector, pBAC108L (3). This was determined by comparing the relative loss of the plasmid in yeast and bacteria in non-selective media.

Figure 2A:
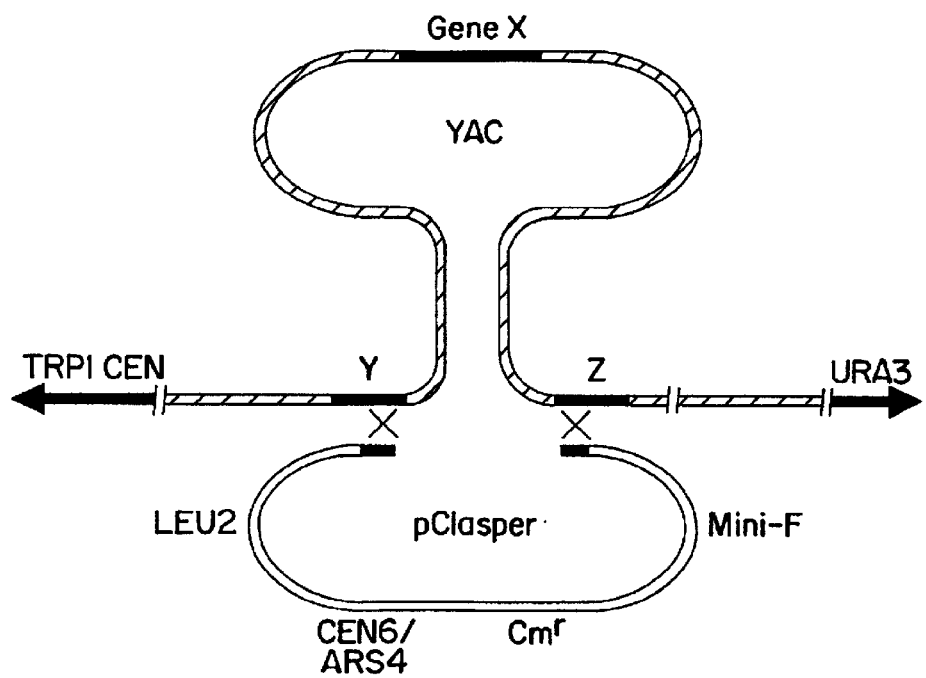
FIG. 2. Schematic representation of homologous recombination between pCLASPER and a YAC. A. The YAC (hatched lines) containing hypothetical Gene X and two known sequences Y and Z (black boxes) recombines with linearized pCLASPER (unfilled lines) at the recombinogenic ends (gray boxes) in the vector. Y and Z can be either sequences in the YAC flanking the region of interest or can be sequences in the YAC arms. B. The result of homologous recombination is a circular product containing the homologous sequences Y and Z and Gene X.
Figure 2B:
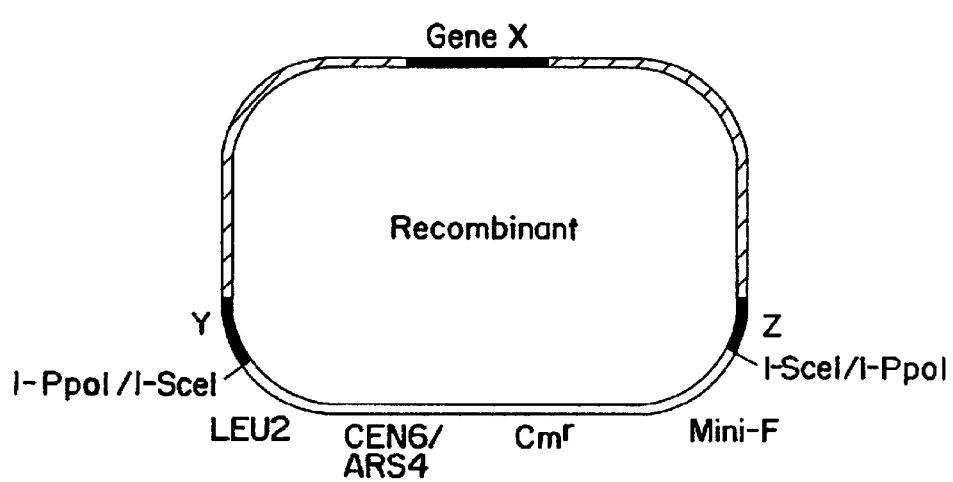

FIG. 2 illustrates one embodiment of the present yeast-bacteria shuttle vector in which the vector is used to isolate specific regions from YACs. The procedure is an extension of yeast gap-repair where free ends of a linear vector recombine with homologous sequences in a chromosome (18). The result of recombination is a circular product with a copy of the sequences from the chromosome maintained between the recombinogenic ends. To clone specific regions from within a YAC, PCR-generated fragments homologous to sequences flanking the region to be cloned are inserted into the shuttle vector. The vector is linearized between the inserted fragments to create recombinogenic free ends. The linear vector is transformed into yeast carrying the YAC in the appropriate genetic background. The circular recombination product is selected for by the acquisition of the yeast auxotrophic marker gene, such as the LEU2 gene carried on the shuttle vector. The specific recombination event is identified by PCR. The recombinant DNA is then shuttled to bacteria for preparation and analysis of plasmid DNA.

The vectors of the present invention may be used to capture large DNA fragments for further analysis. Example of such uses are the capture, manipulation and cloning of YAC DNAs. YACs have become important tools for cloning large genomic regions. Their large size allows for the analysis of large genes or gene clusters. However, it can be laborious to isolate enough YAC DNA from yeast to effectively undertake functional analyses. In addition, YACs frequently contain more genomic DNA than is necessary for function. The present yeast-bacteria shuttle vector circumvents these problems. This vector is used to clone specific regions from YACs and is capable of maintaining large genomic inserts stably in both yeast and bacteria, allowing for mutagenesis in yeast and rapid DNA preparation in bacteria.

The vector of the present invention is used to isolate large subregions of YACs using homologous recombination in yeast. For example, a 27 kb region containing the Hoxc-8 gene has been cloned from a 440 kb Hoxc YAC. Also, the entire insert of 130 kb from a Hoxb YAC has been isolated, producing a stable circular product containing the entire Hoxb cluster.

The procedure by which YAC sequences are isolated is one embodiment of the present invention is related to yeast gap-repair (18) in which free ends recombine with homologous regions in a yeast chromosome resulting in a circular product with the sequences from the chromosome contained between the recombinogenic ends. This general method has been extended to isolate large regions of DNA.

In the present invention, recombinogenic ends may be generated by PCR. Specific recombinants may be recovered using homologous sequences. Recombinogenic ends can easily be used, preferably between 50 bp and 500 bp in size. More preferably, recombinogenic ends of the size 200–500 bp are used. The circular vector containing the large YAC derived insert may be transferred directly from yeast DNA into bacteria. No rearrangements of the DNA are detected in bacteria using the present vector. Additional recognition sites have been added for the intron-encoded endonucleases, I-PpoI and I-SceI, to the polylinker to facilitate the production of large amounts of linear DNA for the generation of transgenic mice and the analysis of the integrity and copy number of the transgenes in the mouse genome. These recognition sites may vary in size. A preferred size is between 8–30 bp. In addition, the polylinker of the vector of the present invention allows for simplified cloning of recombinogenic end fragments and for mapping of the genomic insert.

Inserts between 1 kb and 300 kb in size can be efficiently cloned using the vector of the present invention. Stable large inserts have been obtained in bacteria by using the F factor replicon in the present vector instead of a multicopy origin of replication. Unlike cosmid origins of replication, the F-factor replicon maintains the plasmid as a single copy, thereby preventing recombination between identical copies of a large insert. Structural stability of the large inserts has also been observed in yeast. No rearrangements have been identified in the 27 kb insert. Similar stability has been observed in yeast with inserts of 40 kb and 60 kb. The 130 kb insert is also structurally stable when handled carefully by maintaining selection and limiting passaging of the cells. In the absence of these precautions, some rearrangements of this recombinant may occur. Larger fragments of exogenous DNA are generally believed to be more stable when replicating as linear instead of circular DNA (24, 25).

The methods outlined herein are generally useful in any laboratory with a general knowledge of molecular biology techniques. The only specialized technique performed was tetrad dissection to obtain yeast strains containing the YACs in the appropriate genetic background. Spencer et al (27) have reported an alternative efficient method that takes advantage of the properties of yeast karyogamy mutants for transferring YACs to a new host. This technique requires replica plating rather than tetrad dissection to isolate YAC containing strains of the appropriate genetic background.

Since the vector of the present invention is stably maintained in yeast, homologous recombination can be used to add reporter genes or for mutagenesis of the inserts (28). By transferring the regions of interest from a DNA to the present vector and selecting against the presence of the original DNA, selectable markers can be used for targeted mutagenesis of the selected regions before transformation into bacteria. For example, the lacZ gene was inserted in the Hoxc-8 gene in the pClC9C6 recombinant by homologous recombination and generated β-galactosidase expressing transgenic embryos that recapitulate the endogenous Hoxc-8 expression pattern.

The vector can also be used to transfer DNA contained in other bacterial vectors, such as cosmids PACs, BACs, fosmids or P1, into yeast. It can be difficult to modify larger DNA inserts maintained in bacterial vectors when appropriate restriction sites are unavailable. If the region of interest can be transferred into yeast cells, the researcher can easily introduce more than one specific change by genetic means. Others have shown that DNA can be cloned efficiently into yeast by co-transforming the DNA of interest with linearized vectors containing yeast replicons and appropriate regions of homology. Erickson et al. (29) have co-transformed lambda clones and a yeast-bacteria shuttle vector to isolate specific genes by gap-repair. Ketner et al. (30, 31) have generated YAC clones with high efficiency by co-transforming the 36 kb adenovirus 2 genome with YAC arms.

An additional use of the vector is to clone specific genomic DNA regions by transforming into yeast the linearized vector with total genomic DNA. By this method the present vector may be used to isolate hemizygous templates from pooled DNA samples of individuals. In addition, haplotyping analysis may be carried out.

The utility of the present vector lies in its ability to make homologous recombination in yeast accessible for large genomic fragments cloned by either the methods described herein or by conventional in vitro ligation and bacterial transformation. In addition to the generation of transgenic mice as described above, the vector can also be used for making targeting constructs for the production of mutant mice by homologous recombination in embryonic stem (ES) cells. The ability to introduce the desired changes in yeast will be especially useful when researchers want to move from the disruption of genes in the mouse germ line (knock-out) to the introduction of specific mutations (knock-in) (32). Miller et al (23) identified a gene responsible for a vulval mutant in *C. elegans* by rescue with transgenes made by recombinational cloning from YACs. Similarly, the present vector facilitates the identification of new genes and gene function by transgenic analysis in various organisms and by transfection of tissue culture cells.

All articles and patents referred to herein are incorporated, in toto, by reference.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applications such specific embodiments without departing from the generic concept, and therefore such adaptations and modifications are intended to be comprehended within the meaning and range of equivalents of the disclosed embodiments.

EXAMPLE 1

Construction of Shuttle Vector

The vector, pCLASPER (FIG. 1), was constructed as follows. The PmlI site in pRS415 (Stratagene) was cleaved to insert a linker with a SacI site flanked on one side with a 10 bp reduplication of centromeric DNA from chromosome VI (CEN6) and with a random sequence on the other side to ascertain the orientation by PCR after cloning. The resultant plasmid was cleaved at the BamHI site in the polylinker of pRS415 and at a single DraIII site between the polylinker and the beta-isopropyl malate dehydrogenase gene (LEU2) to insert a 100 bp synthetic DNA fragment containing part of a newly designed polylinker. The new plasmid was digested with SacI and BamHI to isolate the CEN6/ARS4 origin of replication, the LEU2 gene, and one half of the new polylinker. Plasmid pBCSK (Stratagene) was used as a substrate to generate by PCR a 1103 bp fragment encompassing, the chloramphenicol acetyl transferase (Cm$^r$) gene from Tn9. The PCR primer for the 5' end of the gene corresponded to the sequence 1901 to 1921 from pBCSK and contained a 40 bp linker with a SacI restriction site, a BamHI site and another fragment of the new polylinker. The downstream PCR primer corresponded to coordinates 2881 to 3001 of pBCSK and contained a linker with 20 bp of the 5' end of the region of the mini-F gene between BstNI in position 44.2 and NspI in position 443 of the coordinate map of the F-plasmid (4). In a second round of PCR with 80 bp primers containing NspI sites at their 5' end, the ends of the initial PCR product were extended to provide at the 5' end of the Cm$^r$ gene the other half of the new polylinker and at the 3' end the full 100 bp BstNI-NspI fragment necessary for stability of the final mini-F fragment (4). A 53 kb NspI-NspI fragment was isolated from the pOF216 plasmid (5; ATCC). This fragment encompasses the mini-F region from position 443 to 49.4 and was ligated to the final Cm$^r$ PCR product digested with NspI. To create pCLASPER, the resultant plasmid was cleaved with BamHI and SacI and ligated to the BamHI-SacI CEN6/ARS4-LEU2-polylinker fragment derived from pRS415. pCLASPER is maintained in *E. coli* strain DH1OB (Gibco/BRL).

EXAMPLE 2

Construction of Targeting Vectors

The YACs to be targeted were obtained from the Princeton mouse genomic YAC library (6). Isolation and characterization of the Hoxb and Hoxc cluster YACs have been previously described (7, 8). The targeting vector designed to clone the Hoxc-8 gene, pClC9C6, was made as follows. PCR primers for the Hoxc-6 gene (9) were designed to the 5' untranslated region of the gene. The 5' primer was: 5'-TAGATCTGTTTGTCTCCCACATGCC-3' (SEQ ID NO:1) and contained a NruI linker. The 3' primer was: 5'-AGGTGGCAGGATAAGGAAGGGTTAG-3' (SEQ ID NO:2) and contained a HindIII linker. The product was 706 bp. The PCR primers for the Hoxc-9 gene (10) were designed to amplify a 624 bp fragment of the 3' untranslated region. The 5' primer was: 5'-CGACAAGGAACAAATCCTAAGCCC-3' (SEQ ID NO:3) and contained a BamHI linker. The 3' primer was: 5'-TGCATTTGCAGCCTGATCCAGCCA-3' (SEQ ID NO:4) and contained a NruI linker. All polymerase chain reactions (PCR) was carried out in a Hybard Omnigene machine. Reactions contained 1× Boehringer Mannheim PCR buffer supplemented with 2.5 mM MgCl$_2$, 0.8 mM dNTPs and 0.5 U Taq Polymerase (Boehringer Mannheim). The Hoxc YAC was used as template. Reaction conditions were 94° 30 s, 55° 30s and 72° 45s for 30 cycles. PCR products were cloned into the T-tailed vector, pCRII (Invitrogen Corporation). The Hoxc-9 BamHI-NruI PCR fragment was excised and ligated head-to-tail at the NruI site of the cloned Hoxc-6 PCR fragment. The 1.4 kb BamHI/HindIII fragment containing the two PCR products was isolated and ligated to pCLASPER digested with the same enzymes to create pClC9C6.

The targeting vector designed to clone the entire insert from a Hoxb cluster YAC, pClYA, was made by overlap PCR as follows. PCR primers were designed to the YAC arms of pYAC4 (11). One set of primers were designed to amplify a region of 484 bp upstream of the single *E. coli* site of pYAC4. The 5' primer was: 5'-TCTCATGTTTGACAGCTTATCA-3' (SEQ ID NO:5) (position 1–23 of pYAC4 in GenBank accession number U01086) and contained a HindIII linker. The 3' primer was: 5'-AGAGTATACTACATAACATAACACA-3' (SEQ ID NO:6) (position 460–484) and contained an NruI linker and a 15 bp overlap with the 5' primer for the downstream pYAC4 sequence. The second set of primers were designed to amplify 494 bp of pYAC4 downstream of the *E. coli* site. The 5' primer was: 5'-TTCAAGGGAATTGATCCTCTACG-3' (SEQ ID NO:7) (position 656–678) and contains an NruI linker and 15 bp of sequence designed to overlap with the 3' upstream primer described above. The 3' primer was: 5'-AAGATTCCGAATACCGCAAGC-3' (SEQ ID NO:8) (position 1130–1150) and contained a BamHI linker. The Hoxb YAC was used as template in PCR conditions which were as described above with the following modifications. After 10 cycles, part of each reaction was diluted 1:10 and 1 µl of each was added to a new reaction containing primers for the 5' upstream and 3' downstream primers. PCR was continued for an additional 25 cycles. The 975 bp product containing both PCR fragments with an NruI site in-between was cloned into pCRII and subsequently digested with BamHI and HindIII and ligated to pCLASPER to create pClYA.

Figure 3:
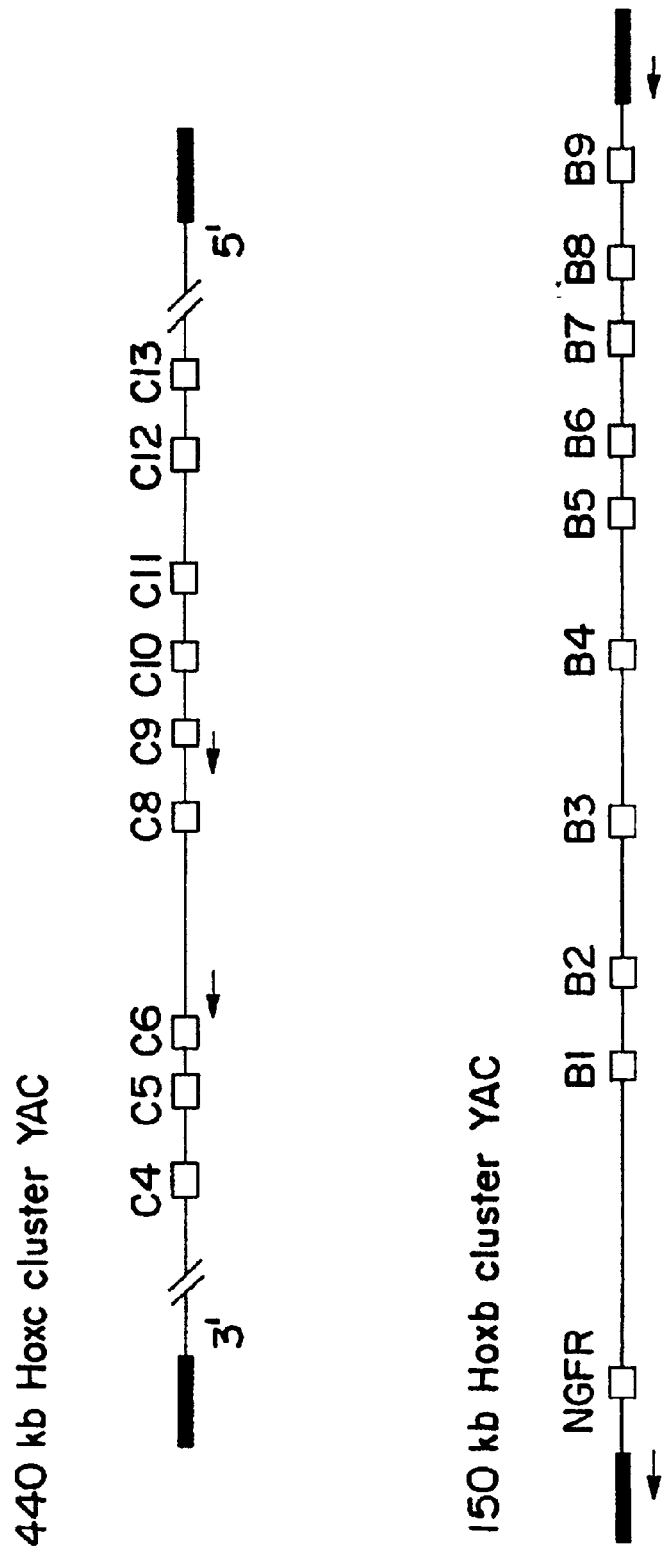
FIG. 3. Schematic representation of Hox cluster YACs. White boxes indicate genes contained on the YACs. Black rectangles represent YAC arms. Both Hox clusters are shown in a 3' to 5' orientation as indicated for Hoxc. All Hox genes are transcribed in the same direction. Arrow heads indicate approximate location and orientation of homologous recombinogenic ends. Recombinogenic ends are 500 bp each, generated by PCR and cloned head-to-tail into pCLASPER to make the specific targeting vectors.

To isolate regions from within a YAC, homologous sequences flanking the region to be targeted are cloned into the polylinker of pCLASPER with a unique restriction site in between for linearization of the vector. These recombinogenic ends were generated by PCR using the YAC to be targeted as template. Two targeting vectors were generated with recombinogenic ends of approximately 500 bp each (FIG. 3). The first was designed to isolate the Hoxc-8 allele from a 440 kb YAC containing the entire Hoxc cluster (8). Recombinogenic ends were designed to be homologous to genomic regions adjacent to the two genes flanking Hoxc-8: Hoxc-9 and Hoxc-6. The targeting vector designed to isolate Hoxc-8, pClC9C6, contained PCR generated ends homologous to the 3' untranslated region of Hoxc-9 and to the 5' untranslated region of Hoxc-6.

The second targeting vector was designed to contain recombinogenic sequences homologous to the arms of pYAC4 (11; FIG. 3). With this vector, the entire insert of any pYAC4 based YAC could be circularized into pCLASPER. This targeting vector, pClYA, was used to isolate a 130 kb region containing the entire Hoxb cluster from a 150 kb YAC (7). The PCR products for the recombinogenic ends for both pClC9C6 and pClYA were inserted head-to-tail into the polylinker of pCLASPER and the vector was linearized at a NruI site designed between the two ends. Linearized DNA was used for LiAc transformation of yeast.

EXAMPLE 3

Preparation of DNA for Yeast Transformations

Since pCLASPER is maintained at single copy, the following procedures facilitate the preparation of large quantities of plasmid DNA. *E. coil* strain DH1OB cells containing the targeting vectors were grown overnight in 1–2 liters TB media containing 20 μg/ml chloramphenicol. Each one liter culture was divided into 3 centrifuge bottles to pellet. The Plasmid Maxi Protocol for Qiagen-tip 500 (Qiagen) was followed for each pellet with the following changes. After the addition of 10 ml each of buffers P1, P2 and P3 to each pellet, the suspension was centrifuged at 4° C. for 30 minutes at 15,000× g. The supernatant was removed, then recentrifuged under the same conditions. The supernatants were pooled, passed through a 0.45 micron filter and loaded on a single Qiagen-tip 500 following the suppliers directions. Generally, at least 20 μg vector DNA per liter of cells was obtained as determined by comparing both optical density and visual estimation on an agarose gel. The targeting vectors, pClC9C6 and pClYA, were both linearized for transformation by extensive over digestion with NruI.

EXAMPLE 4

Yeast Strain Construction

*Saccharomyces cerevisiae* strain AB1380 (MATa, Y+, ura3-52, trpl, canl-100, lys2-1, his5, ade2-1) carrying a YAC containing either the mouse Hoxc (440 kb) or Herb (150 kb) cluster was crossed with strain Y724 (MAT α, ura3-52, lys2-801, ade2-101, leu2-Δ98, trplΔ, his3 Δ200, cyh$^r$, canl$^r$). Diploids were selected by plating on minimal media lacking leucine, histidine and tryptophan. Spores were isolated either by tetrad dissection or hydrophobicity (12) and selected for LEU-, Ura+ and Trp+ phenotypes. The integrity of the YAC in the isolated spores was assessed by pulse field gel electrophoresis (PFGE) and Southern blotting. The resultant strains were YLC44-5 containing the Hoxc YAC and YLB 15-20 containing the Hoxb YAC.

Yeast Transformations

Linearized pClC9C6 (7.5 μg) and pClYA (4 μg) were transformed into strains YLC44-5 and YLB15-20 respectively using a one-step LiAc transformation protocol (13) as follows. The yeast cells were grown overnight in 2 ml of AHC media to log phase. One milliliter of cells was pelleted in a microcentrifuge. 10 μl of 10 mg/ml salmon sperm DNA sheared to an average size of 7 kb and denatured (14) was added to the cell pellet. 10 μl of 1M DTT and 1–10 μg of linear targeting vector was added and the cell pellet was resuspended. 100 μl of one-step buffer (0.2 N LiAc, 40% PEG 4000, pH 5.0) was added and cells were incubated at 45° C. for 30 min. 600 μl of sterile water was added and the cells were spread on drop-out media plates lacking leucine.

Analysis of Recombinants by PCR

Whole cell PCR was performed on yeast colonies to identify recombinants. Individual yeast colonies were first replica plated by streaking in patches onto drop-out media plates lacking leucine. A generous portion of each replica patch was resuspended in 100 μl of sterile water. 10 μl of resuspended yeast was used as template. The primers used to detect recombinants for pClC9C6 were: 1) primer pair in which one primer is specific to the LEU2 region of pCLASPER, 42 bp proximal to the start of the polylinker and the second is specific to the Hoxc-6 5' untranslated DNA in the insert vector primer 5'-TTAAAGAACGTGGACTCCAACG-3' (SEQ ID NO: 9). Hoxc-6 primer 5'-ACTGTGCTCTGCAGTCTCATCCG3' (SEQ ID NO: 10). 2) Primers specific to the second exon of Hoxc-8.5' primer 5'-CGCAGCGGTCGACAAACTTACA-3' (SEQ ID NO: 11); 3' primer 5'-CTCCTCCTCTTTCTCCTCTTCCTA-3' (SEQ ID NO: 12). The primers used to detect recombinants for pClYA were: 1) Vector primer described above with primer specific to pYAC4 in the insert pYAC4 primer 5'-CAACTTGGCTACCGAGAGTA-3' (SEQ ID NO:13) (position 501–520 in pYAC4 in GenBank); and 2) primers specific for the Hox-2.9 gene (Hoxb-1; 7). PCR conditions were as described above except that a 5 minute 94° C. cycle was added prior to the amplification cycles to lyse the yeast cells and 45 amplification cycles were used. When total yeast DNA or bacterial minipreps were used as template, PCR conditions were as described in the construction of the vector.

Electroporation of Bacteria

Yeast carrying the recombined circular product from the pClC9C6 transformation were grown overnight in liquid drop-out media lacking leucine and total DNA was prepared by standard procedures (15). 0.5 μg of total yeast DNA was mixed with 40 μl of *E. Coli* strain DH1OB cells (Gibco/BRL) then transferred to an ice cold 0.2 cm gapped cuvette. A Biorad Gene Pulser was used for electroporation with the settings: 2.5 kV, 200 ohms, 25 μFD. After electroporation, 1 ml of SOC media was immediately added to the cells which were then grown for 1 hr at 37° C. with shaking. Colonies were selected on plates containing 12.5 μg/ml chloramphenicol.

For the larger recombination product from the pClYA transformation (130 kb) yeast DNA was prepared in 100 μl agarose plugs (16). Three plugs containing approximately 10 μg of DNA each were digested with Gelase (Epicentre Technologies) and dialyzed overnight against 10 mM Tris-HCl, 1 mM EDTA, pH 8.0. 5 μl of dialyzed DNA was used for electroporation.

Field Inversion Gel Electrophoresis (FIGE) and Southern Analysis

Yeast DNA was prepared in agarose plugs as previously described (16). Bacterial DNA was prepared by standard alkaline lysis (17) except that DNA was gently resuspended to avoid shearing the DNA. Restriction enzyme digested samples were run at 200 volts for 18 hours at 10° C. with 1–6 see pulse time and 2:1 forward/reverse ratio using a Switchback Pulse Controller (Hoefer Scientific Instruments). For standard agarose gels, yeast DNA was prepared by standard genomic DNA preparation protocols (15). Following electrophoresis, the DNA was nicked by exposure to 254 nm ultraviolet light, denatured, neutralized and transferred to BAS NC supported nitrocellulose (Schleicher and Schuell, Inc.).

The probe used for hybridization of Hoxc YAC derived DNA was a 272 bp PCR product from the second exon of Hoxc-8. The probe used for hybridization of Hoxb YAC derived DNA was a 250 bp PCR product from the first exon of Hoxb-1. Both probes were radiolabeled using the Megaprime random priming kit (Amersham). Hybridizations were done at a probe concentration of 106 cpm/ml of hybridization buffer (40% formamide, 4× Denhardt's, 4× SSC, 10% dextran sulfate, 0.1% SDS).

EXAMPLE 5

Recombination-Based Cloning of Specific Regions From Within Yeast Artificial Chromosomes In order to select for the LEU2 gene contained in pCLASPER, the YAC needs to be in a yeast strain deficient for that gene. Most YAC libraries are constructed in the strain AB1380 which does not contain the appropriate genetic background. The two yeast strains used were produced by crossing AB1380 carrying the appropriate YAC with Y724 and isolating LEU-spores that maintain the intact YAC. After transformation of linearized recombinant plasmids into these strains, yeast colonies were selected for the acquisition of the LEU+ phenotype and analyzed for the loss of the YAC. The YAC was lost either by successive passaging in the absence of selection for the URA3 and TRP1 markers on the YAC arms (strain YLB 15-20) or when the YAC was very stable, by the addition of the uracil analog 5-fluoroorotic acid (5FOA) which selects against the URA3 marker (strain YLC44-5).

pClC9C6 was transformed into yeast carrying a 440 kb mouse Hoxc cluster YAC (strain YLC4-5). pClYA was transformed into yeast carrying a 150 kb mouse Hoxb YAC (strain YLB15-20). After selection as described above, LEU+, URA– yeast colonies carrying the expected circular recombination product were identified by whole cell PCR using primers that were specific for the junction between the vector and the insert and primers specific for a gene in the insert. For the transformation with pClC9C6, 13 LEU+ colonies were obtained, 3 of which were PCR positive for the circular recombination product. For the transformation with pClYA, 3 of 38 colonies obtained were positive.

Figure 4A:
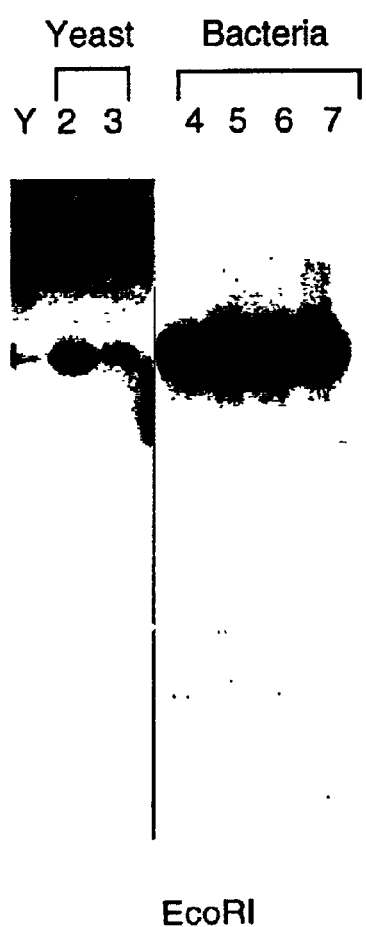
FIG. 4. Southern Analysis of pClC9C6 recombination products. Filters were hybridized with a Hoxc-8 probe. Restriction enzymes used are shown. kb: 1 kb ladder size markers (Gibco/BRL), position and size of marker bands are indicated. Lanes Y: yeast genomic DNA containing Hoxc cluster YAC. Lanes 2, 3, 9 and 10: yeast genomic DNA containing two independent clones of the recombination product of pClC9C6. Lanes 4, 5, 11 and 12: plasmid DNA from two independent clones of bacteria transformed with DNA from the yeast clone in lane 2. Lanes 6, 7, 13 and 14: plasmid DNA from two independent clones of bacteria transformed with DNA from the yeast clone in lane 3.
Figure 4B:
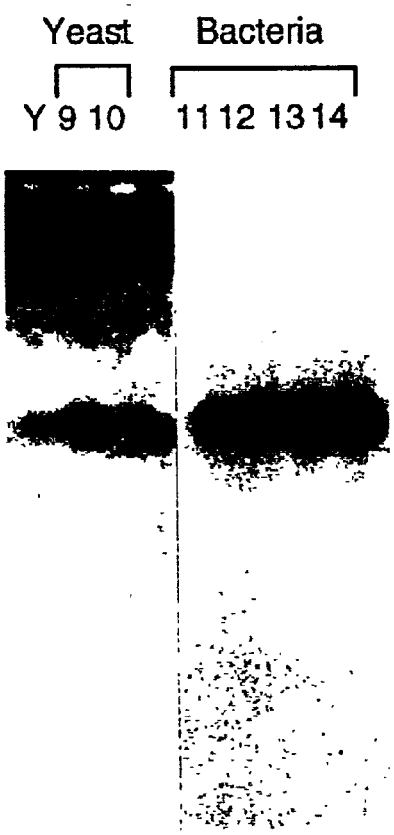

Total genomic DNA was prepared from the PCR positive colonies and reconfirmed by PCR to contain the recombination product. Yeast genomic DNA was used to transform E. coli strain DH1OB by electroporation (21). When bacteria were transformed with the three recombinants of pClC9C6, over 100 chloramphenicol resistant colonies were obtained per transformation. Plasmid DNA from two colonies from each transformation was prepared by standard alkaline lysis procedure (17). Plasmid DNA was digested with either 1-Ppol to release the insert or E. coli. A116 recombinants had the expected insert size (27 kb) and restriction pattern. Southern analysis of two recombinants indicate that in yeast (FIG. 4; lanes 2, 3, 9 and 10) and in bacteria (FIG. 4; lanes 4–7 and 11–14) the recombinants are unrearranged when compared to the original Hoxc YAC (FIG. 4; lanes Y).

Figures 5A, 5B:
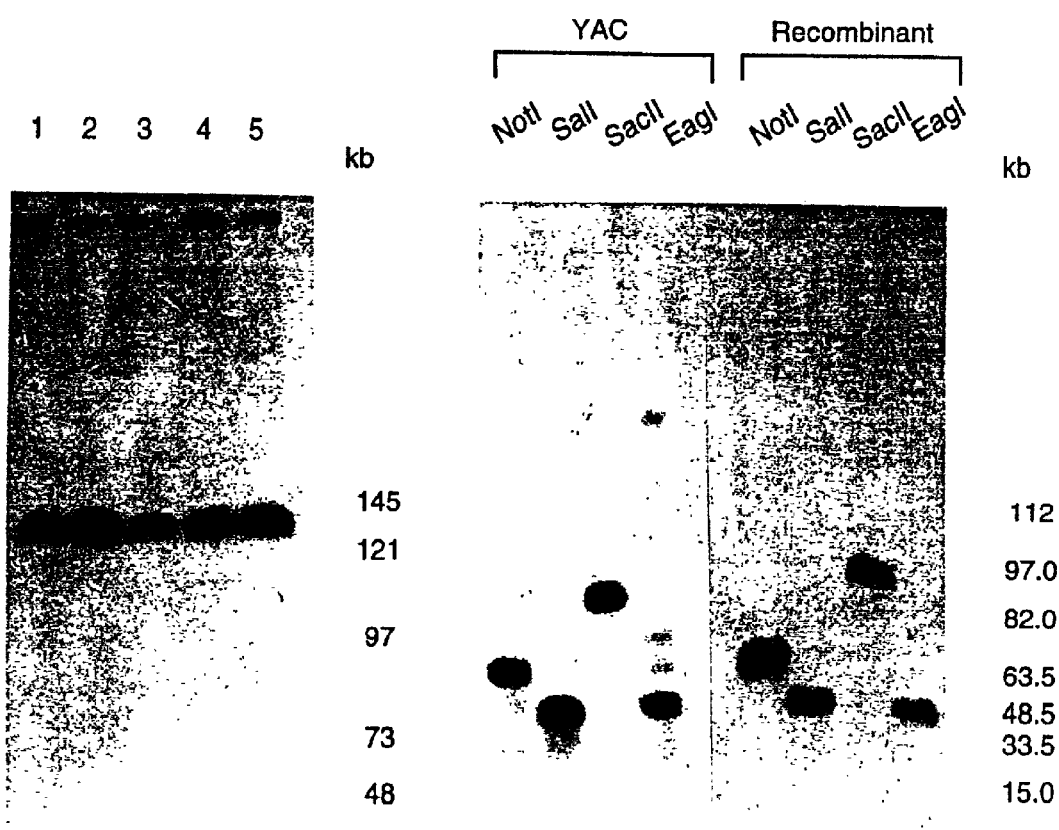
FIG. 5. Southern analysis of pClYA recombination products. Restriction enzyme digested DNA was run by FIGE as described in materials and methods. Filters were hybridized with a probe to Hoxb-1. Panel A: I-PpoI digested plasmid DNA from 5 independent bacterial clones (lanes 1–5) of the recombination product. kb: Midrange PFG Marker II (New England Biolabs), position and size of marker bands are indicated. Panel B. Comparison of restriction digests of the original Hoxb YAC and a recombinant. Yeast genomic DNA containing the YAC was prepared as described in Example 1. Plasmid DNA of recombinant was prepared by standard alkaline lysis. Restriction enzyme used is indicated above each lane. kb: Midrange PFG Marker I (New England Biolabs), position and size of marker bands are indicated.

The recombination product for the pClYA transformation was expected to be approximately 130 kb in size since the recombinogenic ends were homologous to the arms of a 150 kb Hoxb YAC. When total yeast genomic DNA was prepared by standard alkaline lysis methods, the DNA was PCR positive for the recombinant product, but failed to produce any chloramphenicol resistant colonies upon transformation into bacteria. It is likely that the large recombination product was sheared during DNA preparation. To circumvent this problem, yeast genomic DNA was prepared from one recombinant in agarose plugs (7). After Gelase digestion of the agarose plugs and dialysis, the DNA was electroporated into bacteria, resulting in over 50 chloramphenicol resistant colonies per transformation. DNA was prepared by standard alkaline lysis from 5 colonies and analyzed by Southern blotting of a field inversion gel (FIGE). Digestion with I-Ppol produced a band of the predicted 130 kb that hybridized to a Hoxb-I probe (FIG. 5A). The insert from all 5 independent bacteria clones was the same size, indicating that the 130 kb insert is extremely stable in bacteria. Southern analysis using several rare-cutting restriction enzymes was used to compare the integrity of the recombinant to the original Hox-b YAC (FIG. 5B). When hybridized with a Hoxk-1 probe, NotI, SalI and EagI produced identical sized bands of 70, 49 and 49 kb respectively in both the YAC and the recombinant. SacII digestion produced a 87 kb band from the YAC and a 97 kb band from the recombinant. The size difference is due to the lack of SacII sites in the pClYA targeting vector, therefore the 10 kb vector is contained in the SacII band from the recombinant. These results indicate that the pCLASPER vector has stably captured an unrearranged 130 kb insert that contains the entire Hoxb cluster.

REFERENCES

1. Campbell, C., Gulati, R., Nandi, A. K., Floy, K., Hieter, P. and Kucherlapati, R. S. (1991) Proc. Natl. Acad. Sci. USA, 88, 5744–5748.
2. Pavan, W. J., Hieter, P. and Reeves, R. H. (1990) Proc. Natl. Acad. Sci. USA, 87, 1300–1304.
3. Shizuya, H., Birren, B., Kim, U. J., Mancino, V., Slepak, T., Tachiiri, Y. and Simon, M. (1992) Proc. Natl. Acad. Sci. USA, 89, 8794–7.
4. Tolun, A. and Helinski, D. R. (1982) Mol. Gen. Genet., 186, 372–377.
5. Hosada, F., Nishimura, S., Uchida, H. and Ohki, M. (1990) Nucleic Acids Res., 18, 3863–3869.
6. Rossi, J. M., Burke, D. T., Leung, J. C. M., Koos, D. S., Chen, H. and Tilghman, S. M. (1992) Proc. Natl. Acad. Sci. USA, 89, 2456–2460.
7. Bentley, K., Bradshaw, M. S. and Ruddle, F. H. (1993) Genomics, 18, 43–53.
8. Bradshaw, M. S. and Ruddle, F. H. (1994) Genomics, 22, 234–236.
9. Erselius, J. R., Goulding, M. D. and Gruss, P. (1990) Development,
10. Coletta, P. L., Shimed, S. M., Chandhuri, C., Muller, U., Clarke, J. P. and Sharpe, P. T. (1991) Mech. Dev., 35, 129–142.
11. Burke, D. T. and Olson, M. Y. (1991) Methods Enzymol., 194, 251–270.
12. Rockmill, B., Lambie, E J. and Roeder, G. S. (1991) Methods Enzymol., 194, 146–148.
13. Chen, D. -C., Yang, B. -C. and Kuo, T. -T. (1992) Curr. Genet., 21, 83–84.
14. Schiestl, R. H. and Giet, R. D. (1989) Curr. Genet., 16, 339–346.
15. Sherman, F. Fink, G. R. and Hicks, J. B. (1986) Laboratory Course Manual for Methods in Yeast Genetics. Cold Spring Harbor Laboratory Press, Cold Spring Harbor.
16. Bentley, K., Bieberich, C. and Ruddle, F. H. (1990) In Karam, J., Chao, L. and Warr, G. (ed.), Methods in Nucleic Acids Research. CRC Press, Boca Raton, Vol. pp. 131–156.
17. Sambrook, J., Fritsch, E. F. and Maniatis, T. Molecular Cloning: A Laboratory Manual (Cold Spring Harbor Laboratory Press, Cold Spring Harbor, 1989).
18. Orr-Weaver, T. L. and Szostak, J. W. (1983) Proc. Natl. Acad. Sci. USA, 80, 4417 4421.
19. Kline, B. C. (1985) Plasmid, 14, 1–16.
20. Sikorski, R. S. and Hieter, P. (1989) Genetics, 122, 19–27.
21. Dower, W. J., Miller, J. F. and Ragsdale, C. W. (1988) Nucleic Acids Res., 16, 6127–45.
22. Garza, D., J. W. Ajioka, Burke, D. T. and Hartl, D. L. (1989) Science, 246, 641–46.
23. Miller, L. M., Gallegos, M. E., Morisseau, B. A. and Kim, S. K. (1993) Genes Dev., 7, 933–947.
24. Hieter, P., Mann, C., Snyder, M. and Davis, R W. (1985) Cell, 40, 381–92.
25. Murray, A. W., Schultes, N. P. and Szostak, J. W. (1986) Cell, 45, 529–536.
26. McGonigal, T., Bodelle, P., Schopp, C. and Sarthy, A. V. (1995) Gene, 155, 267–271.
27. Spencer, F., Hugerat, Y., Simchen, G., Hurko, O., Connelly, C. and Heiter, P. (1994) Genomics, 22, 118–126.
28. Peterson, K. R., Li, Q. L, Clegg, C. H., Furukawa, T., Navas, P. A., Norton, E J., Kimbrough, T. G. and Stamatoyannopoulos, G. (1995) Proc. Natl. Acad. Sci. USA, 92, 5655–5659.

29. Erickson, J. R. and Johnston, M. (1993) *Genetics,* 134, 151–157.
30. Ketner, G., Spencer, F., Tugendreich, S., Connelly, C. and Hieter, P. (1994) *Proc. Natl. Acad. Sci. USA,* 91, 6186–6190.
31. Spencer, F., Ketner, G., Connelly, C. and Hieter, P. (1993) *Methods: A companion to Methods Enzymol,* 5 161–175.
32. Nagy, A. and Rossant, J. (1995) *Nature Medicine,* 1, 592–594.
33. Beggs, J. D. (1978) *Nature,* 275 104–109.
34. Struhl, K., et al. (1979) *Proc. Natl. Acad. Sci USA,* 76 1035–1039.
35. Pavan, W. J. et al. (1990) *Proc. Natl. Acad. Sci USA,* 87 1300–1304.
36. Campbell, C. et al. (1991) *Proc. Natl. Acad. Sci. USA* 88 5744–5748.
37. Miller, L. M. et al. (1993) *Genes & Devel.* 7 933–947.
38. Kline, B. C. (1985) *Plasmid* 14 1–16.

We claim:

1. A method of producing a transgenic, non-human mammal having integrated into its genome a defined segment of DNA, comprising:
   a. obtaining a yeast-bacteria shuttle vector comprising a yeast replication origin, a yeast selection marker gene, a bacterial replication origin, a bacterial selection marker gene, at least one unique cloning site, and sequences homologous to sequences flanking the defined segment of DNA, wherein said bacterial replication origin is selected from the group consisting of P1 replicon and F factor origin of replication;
   b. linearizing the vector within the homologous sequences to form recombinogenic ends;
   c. introducing the linearized vector into a yeast cell containing DNA comprising the defined segment of DNA, wherein the linearized vector and defined segment of DNA homologously recombine to form a recombinant product;
   d. selecting for the recombinant product;
   e. transferring the recombinant product to bacteria for amplification;
   f. isolating the defined segment of DNA from the recombinant product;
   g. integrating the defined segment of DNA into the genome of a mammal by microinjection of a fertilized egg;
   h. transferring the fertilized egg containing the defined segment of DNA to a pseudopregnant non-human mammal; and
   i. allowing the fertilized egg containing the defined segment of DNA to develop into a transgenic, non-human mammal.

2. The method of claim 1, wherein the defined segment of DNA is mutated by yeast genetics.

3. The method of claim 1, wherein the defined segment of DNA is mutated in bacteria.

4. The method of claim 1, wherein said transgenic mammal is a mouse.

5. The method of claim 1, wherein the yeast-bacteria shuffle vector is pCLASPER.

6. A method of producing a transgenic mouse having integrated into its genome a defined segment of DNA, comprising:
   a. obtaining a yeast-bacteria shuttle vector comprising a yeast replication origin, a yeast selection marker gene, a bacterial replication origin, a bacterial selection marker gene, at least one unique cloning site, and sequences homologous to sequences flanking the defined segment of DNA, wherein said bacterial replication origin is selected from the group consisting of P1 replicon and F factor origin of replication;
   b. linearizing the vector within the homologous sequences to form recombinogenic ends;
   c. introducing the linearized vector into a yeast cell containing DNA comprising the defined segment of DNA, wherein the linearized vector and defined segment of DNA homologously recombine to form a recombinant product;
   d. selecting for the recombinant product;
   e. transferring the recombinant product to bacteria for amplification;
   f. isolating the defined segment of DNA from the recombinant product;
   g. integrating the defined segment of DNA into a specific site in the genome of embryonic stem cells by homologous recombination;
   h. isolating the embryonic stem cells having integrated into their genome the defined segment of DNA;
   i. injecting the embryonic stem cells of step (h) into a blastocyst;
   j. transferring the blastocyst to a pseudopregnant mouse and allowing the blastocyst to develop into a chimeric mouse;
   k. identifying the chimeric mouse that has integrated into its genome the defined segment of DNA;
   l. breeding the chimeric mouse to identify offspring comprising the defined segment of DNA in its germ line; and
   m. breeding the germ-line transmitting offspring to produce a transgenic mouse having integrated into its genome the defined segment of DNA.

7. The method of claim 6, wherein the defined segment of DNA is mutated by yeast genetics.

8. The method of claim 6, wherein the defined segment of DNA is mutated in bacteria.

9. A method for establishing a transgenic, non-human mammalian line comprising: producing a transgenic, non-human mammal according to the method of claim 1 and further breeding the transgenic, non-human mammal to establish a transgenic, non-human mammalian line.

10. The method of claim 6, wherein the yeast bacteria shuttle vector is pCLASPER.

* * * * *